US007450902B2

(12) United States Patent
Crivelli

(10) Patent No.: US 7,450,902 B2
(45) Date of Patent: Nov. 11, 2008

(54) CONTINUOUS PHASE FREQUENCY SHIFT KEYING MODULATION DURING WIRELESS TRANSMISSIONS IN A CLOSED SYSTEM WHILE MINIMIZING POWER CONSUMPTION

(75) Inventor: Rocco Crivelli, Bellinzona (CH)

(73) Assignee: Codman Neuro Sciences Sárl, LeLocle (CH)

(*) Notice: Subject to any disclaimer, the term of this patent is extended or adjusted under 35 U.S.C. 154(b) by 531 days.

(21) Appl. No.: 11/280,084

(22) Filed: Nov. 16, 2005

(65) Prior Publication Data

US 2007/0112397 A1    May 17, 2007

(51) Int. Cl.
    *H04B 5/00*    (2006.01)
(52) U.S. Cl. .................. 455/41.1; 455/113; 375/272
(58) Field of Classification Search .................. None
    See application file for complete search history.

(56) References Cited

U.S. PATENT DOCUMENTS

| | | | |
|---|---|---|---|
| 3,843,839 A | | 10/1974 | Campbell et al. |
| 4,316,472 A | | 2/1982 | Mirowski et al. |
| 4,561,443 A | | 12/1985 | Hogrefe et al. |
| 4,847,617 A | | 7/1989 | Silvian |
| 5,235,326 A | | 8/1993 | Beigel et al. |
| 5,499,017 A | | 3/1996 | Beigel |
| 5,673,018 A | * | 9/1997 | Lowe et al. ................ 455/41.1 |
| 5,999,857 A | | 12/1999 | Weijand et al. |
| 6,106,551 A | | 8/2000 | Crossett et al. |
| 6,201,993 B1 | | 3/2001 | Kruse et al. |
| 6,427,088 B1 | | 7/2002 | Bowman et al. |
| 6,482,154 B1 | | 11/2002 | Haubrich et al. |
| 6,529,127 B2 | | 3/2003 | Townsend et al. |
| 6,567,703 B1 | | 5/2003 | Thompson et al. |
| 6,611,198 B1 | * | 8/2003 | Geiszler et al. .......... 340/10.41 |
| 6,801,807 B2 | | 10/2004 | Abrahamson |
| 2003/0065308 A1 | | 4/2003 | Lebel |

OTHER PUBLICATIONS

"Demodulation of CPFSK and GMSK Signals using Digital Signal Processing DPLL . . . ", Iwanami, Y., IEICE Trans. Commun., vol. 84-B, No. 1, pp. 26-35, Jan. 2001.
Sanyal S. K. et al., "New Active-R Sine Wave Oscillators . . . ", International Journal of Electronics, vol. 70, No. 1, Jan. 1991, pp. 139-149.
Website, "http://www.elecdesign.com/Articles/Index.cfm?AD=1 &ArticleD=6337" (5 pp.) (Jun. 8, 2005).

* cited by examiner

*Primary Examiner*—Thanh C Le
(74) *Attorney, Agent, or Firm*—Cheryl F. Cohen, LLC

(57) ABSTRACT

Continuous phase frequency shift keying modulation is employed during wireless transmission from an internal device to an external device to increase robustness of transmissions. The continuous phase frequency shift keying processor receives as input an incoming data stream and includes a timer for toggling its output between a first predetermined frequency and a second predetermined frequency on a predetermined time period basis based on the logical state of each bit in the incoming data stream. For a portion of time while the counter or timer of the CPFSK processor is counting down the predetermined time period associated with the detected logic state of a particular bit of the incoming data signal at least some of the other circuitry, preferably all of the other circuitry of the processor, is toggled to a sleep mode in which power is cut off thereby minimizing power consumption by the processor during this interim state.

18 Claims, 3 Drawing Sheets

CONTINUOUS PHASE FREQUENCY SHIFT KEYING MODULATION DURING WIRELESS TRANSMISSIONS IN A CLOSED SYSTEM WHILE MINIMIZING POWER CONSUMPTION

BACKGROUND OF THE INVENTION

1. Field of the Invention

The present invention is directed to continuous phase frequency shift keying modulation for use in a wireless communication system. In particular, the invention relates to continuous phase frequency shift keying modulation generated during wireless transmissions using a dedicated processor in a closed system. One specific application of the present invention is for wireless communication from an implantable medical device to an external control device in a closed system, wherein the implantable medical device employs a processor dedicated exclusively to generating continuous phase frequency shift keying modulation during uplink wireless communication to the external device while minimizing energy consumption.

2. Description of Related Art

The use of frequency shift keying as a modulation technique is well known and widely used in a large number of different applications. One such application is the use of frequency shift keying modulation during telemetric communications between an external control device and an implantable medical device. For instance, U.S. Pat. No. 4,561,443 discloses a two-way inductive communications link between an external transceiver 32 and an internal transceiver 34 located in a biologically implanted programmable infusion pump (IPIP). Communication from the external transceiver 32 to the IPIP utilizes frequency shift keying at 48.0 kHz and 51.2 kHz while the return communications link from the IPIP utilizes frequency shift keying between AM subcarriers at 1.6 kHz and 3.2 kHz. Both the external and implant sides of the patented device use a physical switch to toggle between the two frequencies. Specifically, external transceiver 32 includes a switch 40 driven by a power driver 44 to toggle between a first crystal oscillator 38 operating a 48.0 kHz and a second crystal oscillator 35 operating at 51.2 kHz. On the implant side, IPIP transceiver 34 also employs a switch 72 for toggling between a first carrier frequency of 1.6 kHz and a second carrier frequency of 3.2 kHz, wherein a timing and control unit 70 is employed to control the switch 72. The use of a physical switch in the design configuration requires a driving signal to toggle between the two carrier frequency states. While generating the FSK modulated signal on either the implant or external side there is no way to ensure perfect synchronization (e.g., zero phase) when switching between the oscillators, thereby resulting in phase discontinuities in the FSK modulated output signal. An illustrative example of a discontinuous phase FSK modulation signal is shown in FIG. 1. A "0" or low bit is represented by a first frequency $f_0$ while a "1" or high bit is represented by a second frequency $f_1$, wherein the first frequency $f_0$ is lower than that of the second frequency $f_1$. The example signal shown in FIG. 1 includes multiple periods, e.g., $Tf_0$, $Tf_0'$, $Tf_1$, $Tf_1'$. As seen in FIG. 1 phase discontinuities are present, e.g., the time period $Tf_0$ and $Tf_0'$ are not equal, while the time period $Tf_1$ and $Tf_1'$ are also not equal. Referring to the specific example depicted in FIG. 1, the phase discontinuity occurs due to the early transition from the low to the high frequency early during the time period $Tf_0'$ (as indicated by the dashed line). As a result of this discontinuity in phase of the FSK modulation signal the wireless transmission is less robust having a negative impact on the demodulation of the recovered signal.

It is therefore desirable to develop circuitry in a closed system employing continuous phase FSK (CPFSK) modulation during wireless communication to improve the robustness and sensitivity of transmissions while minimizing power consumption.

SUMMARY OF THE INVENTION

An object of the present invention is to provide circuitry in a closed system for producing a CPFSK modulated signal using a dedicated processor.

Another object of the present invention to provide circuitry for employing CPFSK modulation while minimizing power consumption.

Yet another object of the present invention is to employ CPFSK modulation so as to increase the robustness of transmission of the demodulated signal therefrom.

Still another object of the present invention is to transmit a CPFSK modulated signal during uplink wireless transmission from an internal device to an external device of a closed system while eliminating the need for an active emitter on the implant side.

Continuous phase frequency shift keying modulation is employed during wireless transmission from an internal device to an external device to increase robustness of transmissions. The continuous phase frequency shift keying processor receives as input an incoming data stream and includes a timer for toggling its output between a first predetermined frequency and a second predetermined frequency on a predetermined time period basis based on the logical state of each bit in the incoming data stream. For a portion of time while the counter or timer of the CPFSK processor is counting down the predetermined time period associated with the detected logic state of a particular bit of the incoming data signal at least some of the other circuitry, preferably all of the other circuitry of the processor, is toggled to a sleep mode in which power is cut off thereby minimizing power consumption by the processor during this interim state.

The present invention is directed to a closed system including an external device separated by a boundary from and in wireless communication with an internal device, for example, an implantable medical device. The internal device including a continuous phase frequency shift keying processor for receiving an incoming data stream, wherein the continuous phase frequency shift keying processor includes a timer for toggling its output between a first predetermined frequency and a second predetermined frequency on a predetermined time period basis based on the logical state of each bit in the incoming data stream. Specifically, the continuous phase frequency shift keying processor includes circuitry, other than the timer, at least some of which is adapted to toggle to a sleep mode without power for a portion of the predetermined time period thereby minimizing the energy consumed by the internal device. Prior to the expiration of the predetermined time period, preferably approximately halfway in the countdown of the predetermined time period, the processor issues a timer based interrupt signal to power on the circuitry in sleep mode in preparation for the next bit in the incoming data stream. As a result of the toggling of at least some of the circuitry associated with the processor to a sleep mode during the interim period in which the timer is counting down the predetermined time period, the continuous phase frequency shift keying processor may be powered exclusively via an external RF signal generated during communication from the external device to the internal device.

Furthermore, the invention is directed to a method for minimizing energy consumption of a continuous phase frequency shift keying modulation processor for use in a closed system, as described in the preceding paragraph. The method includes the steps of toggling of an output signal of the continuous phase frequency shift keying modulation processor between a first predetermined frequency and a second predetermined frequency on a predetermined time period basis based on a logical state of each bit in an incoming data stream to the continuous phase frequency shift keying modulation processor. Specifically, initially a logical state of a first bit of the incoming data signal to the internal device is detected. Based on the detected logical state of the first bit of the incoming data signal: (i) a continuous phase frequency shift keying encoded output signal is generated at one of a first predetermined frequency or a second predetermined frequency; and (ii) a predetermined time period of the timer of the continuous phase frequency shift keying processor is set to a first time period or a second time period. A power down signal is generated to toggle to a sleep mode at least some circuitry of the processor, while the timer associated with the continuous phase frequency shift keying processor remains powered on at all times. Prior to the expiration of the countdown by the timer of the set predetermined time period, preferably approximately half of the countdown of the set predetermined time period for the timer, a timer based interrupt signal is issued to power on the previously powered down circuitry of the processor in sleep mode. The logical state of a next bit from the incoming data stream is monitored. Upon detection of a change of logical state between consecutive bits of the incoming data stream, the frequency and associated time period for the timer are updated. This same process is repeated for each bit in the incoming data stream.

Yet another aspect of the invention is directed to a continuous phase frequency shift keying processor receiving as input an incoming data stream and producing a continuous phase frequency shift keying encoded output signal. The continuous phase frequency shift keying processor includes a timer for toggling the continuous phase frequency shift keying encoded output signal between a first predetermined frequency and a second predetermined frequency on a predetermined time period basis based on the logical state of each bit in the incoming data stream. The invention also relates to a method for minimizing energy consumption of a continuous phase frequency shift keying modulation processor, as described in the preceding paragraph.

BRIEF DESCRIPTION OF THE DRAWINGS

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

The present invention is directed to circuitry for generating in a closed system a continuous phase frequency shift keying (CPFSK) modulated signal using a dedicated wireless processor. One such application discussed in detail in the present invention is the use of the dedicated processor in an implantable medical device for generating a CPFSK modulated signal for uplink wireless transmission to an external device disposed outside the patient's body. It is, however, contemplated and within the intended scope of the present invention to be used for any type of wireless transmission. The use of zero phase crossover CFSK is particularly advantageous during wireless transmissions between devices in a closed system in that it (i) provides smoother transitions from high (e.g.,"1") to low (e.g., "0") bits, (ii) limits the radiated harmonics, and (iii) ensures proper demodulation of the received coded signal by improving the robustness of wireless transmissions.

Often in a closed system, and of particular relevance in an implantable medical device system, a significant parameter in designing the internal device (e.g., implant) is to maximize the longevity of the life of the internal power source associated therewith. Depletion of the stored energy of the internal power source associated with an implantable medical device requires surgery to replace either the power source or implant itself. Accordingly, it is desirable to minimize the power consumed by the internal device in an effort to optimize the lifespan of the internal power source. A substantial amount of energy is consumed by the internal device in generating an FSK modulated signal. The present invention minimizes the energy consumed by the internal device while generating an FSK modulated signal.

Figure 1:
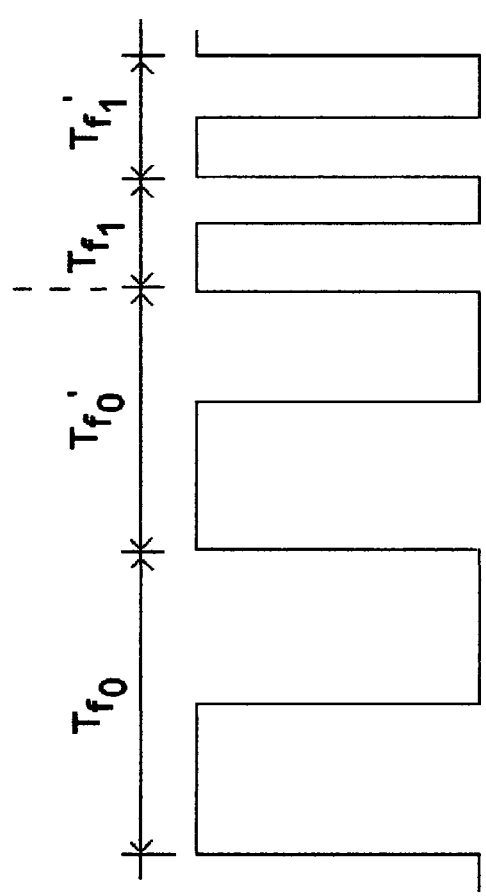
FIG. 1 is an exemplary discontinuous phase frequency shift keying modulation square wave signal, wherein a logical state of "0" is represented by a square signal having a first frequency $f_0$ and a logical state of "1" is represented by a square wave signal having a second frequency $f_1$.
Figure 2:
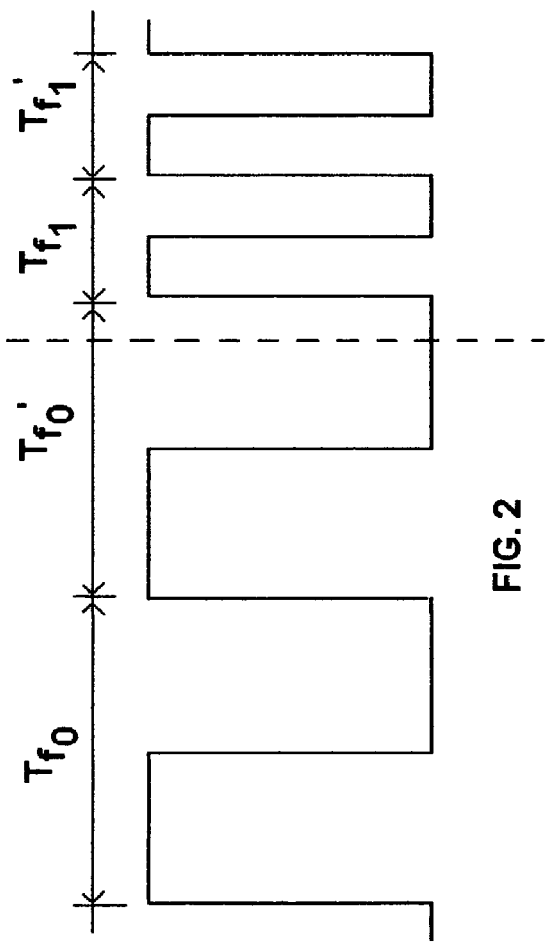
FIG. 2 is an exemplary continuous phase frequency shift keying modulation square wave signal in accordance with the present invention.
Figure 3:
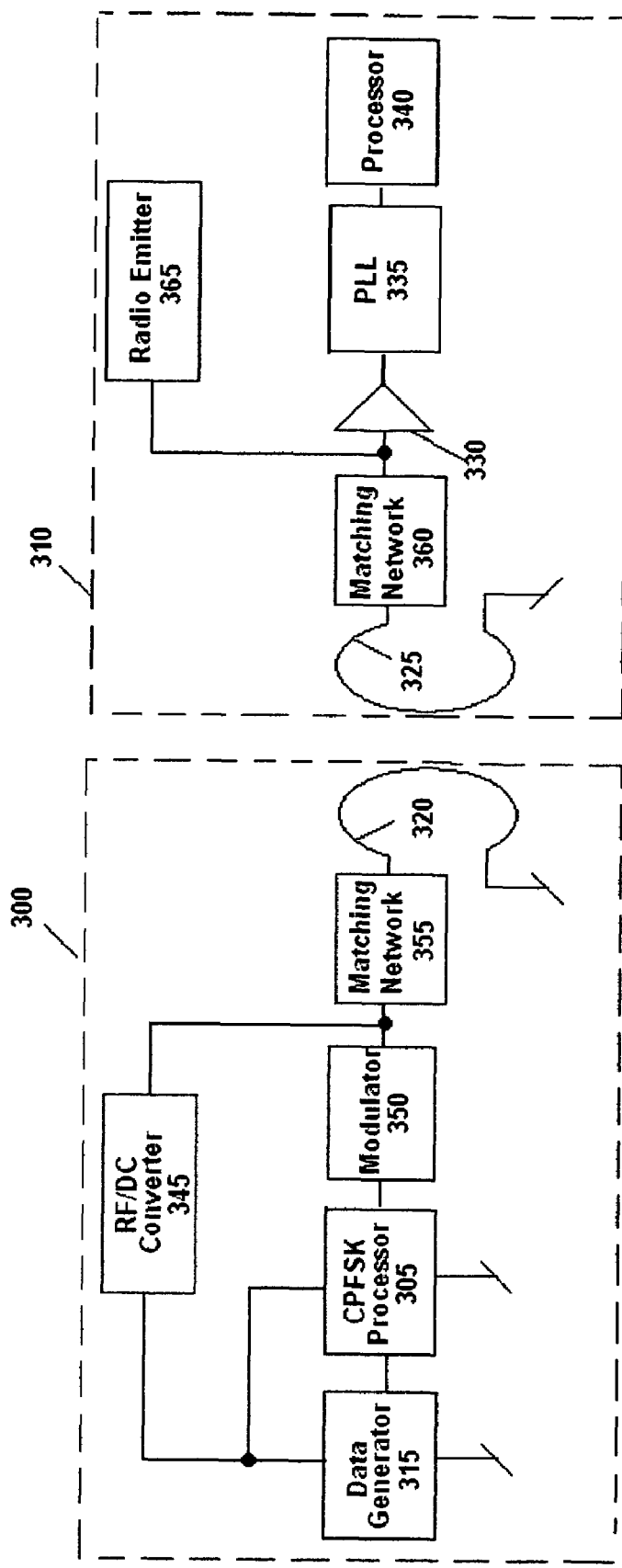
FIG. 3 is an exemplary schematic diagram of a telemetric implantable medical device system including circuitry for producing a continuous phase frequency shift keying modulation signal during uplink communications in accordance with the present invention using a dedicated processor in the implantable medical device.

By way of example, circuitry for producing a CPFSK modulated signal in accordance with the present invention for an implantable medical system is shown in FIG. 3. An implantable medical device (internal device) 300 implanted in a patient is in wireless communication with an external device 310. A CPFSK modulated signal is transmitted during uplink communications from the implantable medical device 300 to the external device 310 to improve the robustness of transmission. In order to produce a continuous zero phase deviation frequency shift keying modulated signal in accordance with the present invention, the use of physical switches for toggling between two different frequencies has been eliminated. Instead, the CPFSK modulated signal is produced using a dedicated processor or controller 305 that receives as input a data stream from data generator 315 and produces a CPFSK encoded signal. Processor 305 includes a variable timer, counter or clock in order to toggle its digital output between a first frequency $f_0$ and a second predetermined frequency $f_1$ on a predetermined interval or period of time basis based on the logical state of bits representing the incoming signal. In a preferred embodiment, only a single dedicated processor 305 is employed to produce the CPFSK modulated signal. It is, however, contemplated and within the intended scope of the present invention, although not preferred due to an increase in energy consumption, to use multiple processors for generating the CPFSK modulated signal.

In addition to the dedicated processor or controller 305 for producing the CPFSK modulated signal, implantable medical device 300 includes other processors, for example, the data generator 315. It is contemplated that additional processors (although not shown in FIG. 3) may, and with most likelihood would, be employed in the implantable medical device 300 for performing functions other than the generation of the CPFSK modulated signal without deviating from the scope of the present invention.

The CPFSK encoded signal from processor 305 is, in turn, received as input to a modulator 350. In the case of passive telemetry, modulator 350 performs absorption modulation of the incoming external RF signal generated by the radio emitter 365 of external device 310 during communication with the implantable medical device 300. The external RF signal from the external device 310 is received by secondary antenna or coil 320, passes through a matching network 355 and is then converted to a DC signal by RF/DC converter 345. In a preferred embodiment, the DC signal output from converter 345 is used to power both the data generator 315 and CPFSK processor 305. On the other hand, in the case of an active communication from the implantable medical device 300 to the external device 310, modulator 350 would include a transmitter emitter. The modulated output signal from block 350 passes through the matching network 355 prior to wireless transmission via the secondary antenna or coil 320 to the external device 310.

A primary antenna or coil 325 on the external device side receives the wireless signal transmitted by the implantable medical device 300 which, in turn, passes through matching network 360 and amplifier 330. The amplified output signal from block 330 is received as input by a phase locked loop (PLL) 335 to demodulate the FSK modulated signal. Then the demodulated signal is received by processor 340 which produces a decoded recovered signal.

Figure 4:
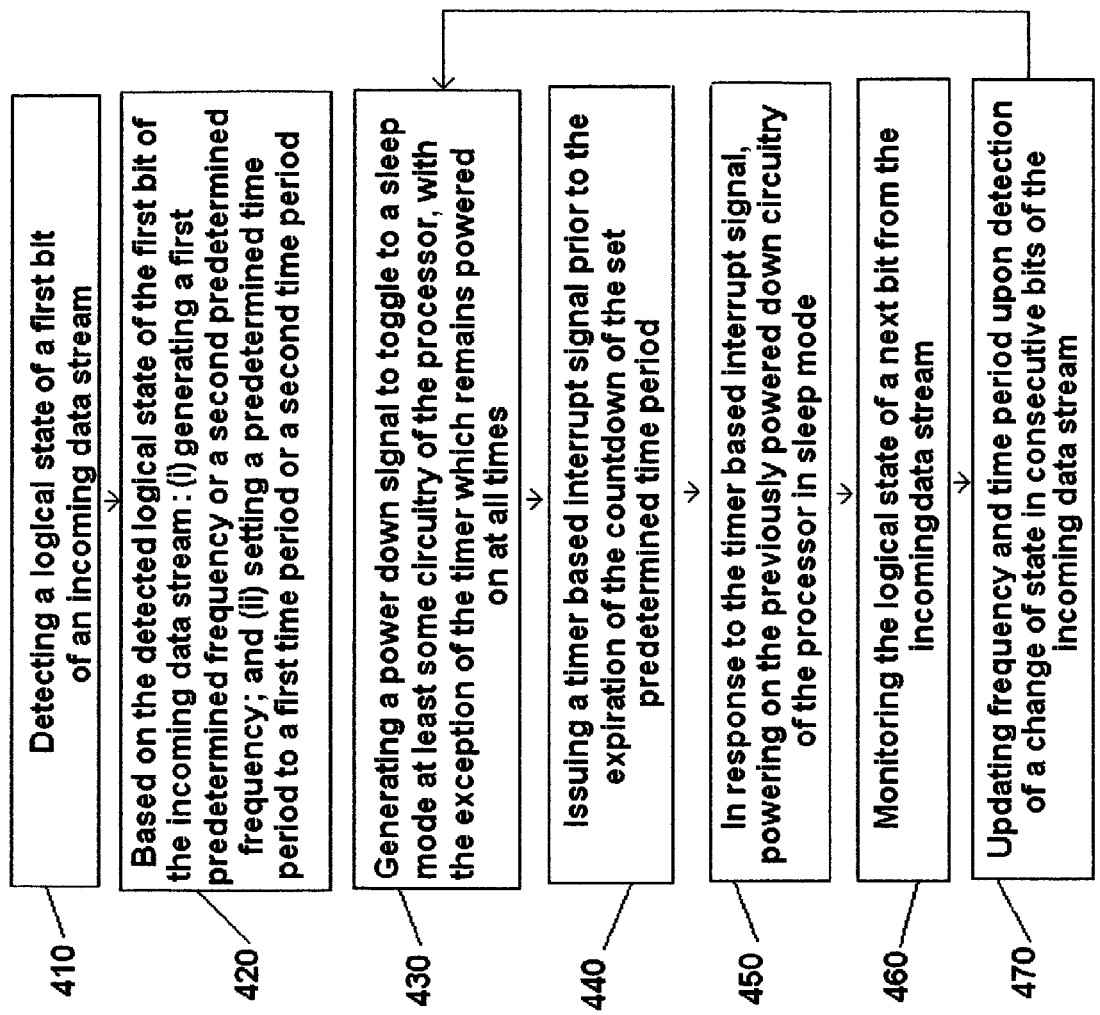
FIG. 4 is an exemplary flow diagram of the process for generating a continuous phase frequency shift keying modulation signal employing a dedicated processor in accordance with the present invention.

FIG. 4 is an exemplary flow diagram of the steps performed by the dedicated processor 305 in generating a CPFSK modulated signal while minimizing power consumption. Processor 305 receives as input an incoming data stream from data generator 315. Initially, in step 410 processor 305 detects a logical state of a first bit of the incoming data stream. In step 420 CPFSK processor 305 by toggling the state of its output pin generates the CPFSK encoded output signal at either a first frequency $f_0$ or a second frequency $f_1$ depending on the detected logical state of the first bit of the incoming data stream. Toggling of the state of the output of processor 305 occurs on a predetermined time period that depends on the logical state of the first bit of the incoming data signal. For example, a "0" or low bit is represented by a first frequency $f_0$ having a first time period $T_{f0}$, while a "1" or high bit is represented by a second frequency $f_1$, having a first time period $T_{f1}$, wherein the first frequency $f_0$ is lower than that of the second frequency $f_1$. Next, in step 430, CPFSK processor 305 initiates a power down signal thereby toggling to a sleep mode (in which power is cut off) at least some of its circuitry, with the exception or exclusion of the timer which remains powered on at all times. By powering down some circuitry of the CPFSK processor 305 its overall power consumption is reduced. The timer begins to count down the predetermined time period associated with the given frequency of the first bit of the incoming data signal. Prior to expiration of the predetermined time period associated with the given frequency of the first bit of the incoming data signal, CPFSK processor 305 generates a timer based interrupt signal in order to wake up (power on) the circuitry of the processor that is in sleep mode in preparation for possible toggling, as represented in step 440. In a preferred embodiment, the CPFSK processor 305 generates a timer based interrupt signal at the expiration or countdown of approximately half the predetermined time period associated with the given frequency of the first bit of the incoming data signal. In response to the timer based interrupt signal, the previously powered down circuitry of the CPFSK processor that is in sleep mode is activated or energized in step 450.

The next bit of the incoming data signal is then monitored or checked by CPFSK processor 305 in step 460 to determine its logical state. A conditional decision is made in step 470 to toggle or update the predetermined frequency of the CPFSK encoded output signal and associated predetermined time period value of the timer when CPFSK processor 305 detects a change of logical state between consecutive bits of the incoming data stream. If no change in logical state is detected then the predetermined frequency of the encoded output signal and the associated predetermined time period of the timer remains unchanged. Otherwise, in the presence of a change in logical state between consecutive bits of the incoming data stream, the output port is toggled to alter the frequency of the CPFSK encoded output signal and the timer is set to its corresponding predetermined time period accordingly. This process repeats itself starting with step 430 for each bit of the incoming data stream. Accordingly, for a portion of time while the counter or timer of the CPFSK processor is counting down the period of time associated with the detected logic state of a particular bit of the incoming data signal at least some of the other circuitry, preferably all of the other circuitry of processor 305, is toggled or switched to a sleep mode in which power is cut off thereby minimizing power consumption by the processor 305 during this interim state.

The process for generating a CPFSK modulated signal using a single dedicated processor in accordance with the present invention will now be described for an exemplary incoming data stream of "0011". Processor 305 is dedicated to generating the CPFSK modulated signal in response to the data stream signal received as input and generated by block 315. A timer associated with the CPFSK processor 305 continuously counts down and remains powered on at all times. A timer based interrupt signal is generated by CPFSK processor 305 at the expiration of approximately half of one of two preset periods of time representative of a first time period $Tf_0$ associated with the first frequency $f_0$ representing a low incoming bit and a second time period $Tf_1$ associated with the second frequency $f_1$ representing a high incoming bit. Initially, CPFSK processor 305 determines the logical state of the first bit of the incoming data stream. In the example discussed herein, the logical state of the first bit is low (e.g., "0"). Accordingly, the timer is set initially to the first time period $Tf_0$ associated with the first frequency $f_0$. The timer then starts counting down the first time period $Tf_0$ during which interim period the CPFSK processor 305 powers down, with the exception of the timer, at least some circuitry (preferably all other circuitry) associated with the processor 305 to a sleep mode in which power is cut off. The timer remains continuously powered at all times even while the other circuitry is powered down in a sleep mode. By toggling some of its circuitry to sleep mode, the amount of energy consumed by CPFSK processor 305 is reduced but never reaches zero since a minimum amount of powered is supplied to maintain continuous operation of the timer. Upon the expiration of approximately half of the first time period ($Tf_0/2$) a timer based interrupt signal is initiated by CPFSK processor 305 and, in response thereto, the processor circuitry previously powered down in sleep mode is activated or awakened while the state of the next bit of the incoming data stream is monitored or checked to determine whether there is a change of logical state.

In the example incoming data stream, the second or next bit of the incoming data signal is also low (e.g., "0"). Since there is no change in state between the first and second bits of the incoming data signal the first frequency $f_0$ is maintained along with its corresponding preset time period $Tf_0'$. Thus, the selected time period for the timer remains unchanged and CPFSK processor 305 issues a powered down signal whereby at least some of the circuitry (with the exception of the timer) once again reverts or toggles back to a sleep mode. As previously mentioned, while in sleep mode, with the exception of the timer, power is cut off from at least some circuitry (preferably all other circuitry) associated with the processor 305. The CPFSK processor maintains this sleep mode state until expiration by the timer of approximately half of the first time period ($Tf_0'/2$) whereby a timer based interrupt signal is generated. Processor 305 then issues an activation signal that awakens or activates the circuitry previously in sleep mode and a check is made of the third or next bit of the incoming signal which in the example is high (e.g. "1"). The detection of a change of state between the second and third bits of the incoming data stream from a high signal to a low signal, causes CPFSK processor 305 to toggle the output pin to a second predetermined frequency $f_1$ representative of a high incoming bit and change the timer or counter value to a corresponding second time period $Tf_1$. Once again CPFSK processor 305 toggles, with the exception of the timer that remains continuously powered, at least some of the other circuitry of the processor to a powered down sleep mode to conserve energy. At the expiration of the countdown of approximately half the second time period ($Tf_1/2$) a timer based interrupt activates or awakens the previously powered down components. Processor 305 monitors or checks the fourth or next bit of the incoming data stream which is high (e.g., "1"). Since the state of the third and fourth bits of the incoming data stream is the same, the counter value representative of the preset time period $Tf_1'$ and frequency $f_1$ remains unchanged while processor 305 toggles to a powered down sleep mode at least some of the circuitry of the processor, with the exception of the timer which remains continuously operational.

Use of FSK modulation during wireless communication is beneficial for several reasons. The demodulation of a frequency encoded signal is possible even when the amplitude of the modulated signal is extremely weak, because the demodulator (usually a PLL) is sensitive to the frequency content of the modulated signal and not to the amplitude. This is not the case for an amplitude modulated signal. Accordingly, the present invention is well suited for the particular application of an implantable medical device of a passive telemetry system in which the amplitude or strength of the signal is relatively weak due to the coupling inefficiency between devices. The use of zero phase crossover CPFSK is even more advantageous in wireless communications in that it smoothes out transitions from "1" to "0", limits radiated harmonics, and ensures proper demodulation of the transmitted coded signal received by the external device from the internal device.

However, the use of FSK modulation typically consumes a substantial amount of power or energy. This is particularly problematic when employed in a system that must optimize or minimize power consumption such as in a closed system. A significant design parameter in an implantable medical device system such as that shown and described above is powering of the internal device and its associated circuitry. In this regard, some if not all, of the power necessary to operate the internal device may be provided by an external radio frequency emission or radiation from the external device during wireless communication with the internal device. However, such limited power as is provided by external RF radiation during wireless transmissions from the external device would not be adequate to perform the FSK modulation using conventional implementations. The present inventive circuitry substantially reduces the amount of energy consumed during FSK modulation to such an extent that it may be powered exclusively by the limited external RF radiation emitted by the external device during communication with the internal device.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A closed system comprising:
    an external device; and
    an internal device separated by a boundary from and in wireless communication with the external device, the internal device comprising:
    a continuous phase frequency shift keying processor for receiving an incoming data stream, the continuous phase frequency shift keying processor including a timer for toggling its output between a first predetermined frequency and a second predetermined frequency on a predetermined time period basis based on the logical state of each bit in the incoming data stream.

2. The system in accordance with claim 1, wherein the internal device is an implantable medical device.

3. The system in accordance with claim 1, wherein the timer remains powered on at all times.

4. The system in accordance with claim 3, wherein the continuous phase frequency shift keying processor includes circuitry, other than the timer, at least some of which is adapted to toggle to a sleep mode without power for a portion of the predetermined time period.

5. The system in accordance with claim 4, wherein prior to the expiration of the predetermined time period, the processor issues a timer based interrupt signal to power on the circuitry in sleep mode.

6. The system in accordance with claim 5, wherein the timer based interrupt signal is generated approximately halfway through the countdown of the predetermined time period.

7. The system in accordance with claim 1, wherein the continuous phase frequency shift keying processor is powered exclusively via an external RF signal generated during communication from the external device to the internal device.

8. A continuous phase frequency shift keying processor receiving as input an incoming data stream and producing a continuous phase frequency shift keying encoded output signal, the processor comprising:

a timer for toggling the continuous phase frequency shift keying encoded output signal between a first predetermined frequency and a second predetermined frequency on a predetermined time period basis based on the logical state of each bit in the incoming data stream.

9. The processor in accordance with claim 8, wherein the continuous phase frequency shift keying processor includes circuitry, other than the timer, at least some of which is adapted to toggle to a sleep mode without power for a portion of the predetermined time period.

10. The processor in accordance with claim 9, wherein prior to the expiration of the predetermined time period, the processor issues a timer based interrupt signal to power on the circuitry in sleep mode.

11. The processor in accordance with claim 10, wherein the timer based interrupt signal is generated approximately halfway through the countdown of the predetermined time period.

12. A method for minimizing energy consumption of a continuous phase frequency shift keying modulation processor in an internal device that wirelessly transmits a continuous phase frequency shift keying modulated signal to an external device across a boundary disposed therebetween, the method comprising the steps of:

toggling an output signal of the continuous phase frequency shift keying modulation processor between a first predetermined frequency and a second predetermined frequency on a predetermined time period basis based on a logical state of each bit in an incoming data stream to the continuous phase frequency shift keying modulation processor.

13. The method in accordance with claim 12, wherein the toggling step comprises the steps of:

(a) detecting a logical state of a first bit of the incoming data signal to the internal device;

(b) based on the detected logical state of the first bit of the incoming data signal: (i) generating a continuous phase frequency shift keying encoded output signal at one of a first predetermined frequency or a second predetermined frequency; and (ii) setting a predetermined time period of a timer of the continuous phase frequency shift keying processor to a first time period or a second time period;

(c) generating a power down signal to toggle to a sleep mode at least some circuitry of the processor, while the timer associated with the continuous phase frequency shift keying processor remains powered on at all times;

(d) prior to the expiration of the countdown by the timer of the set predetermined time period, issuing a timer based interrupt signal to power on the previously powered down circuitry of the processor in sleep mode;

(e) monitoring the logical state of a next bit from the incoming data stream;

(f) updating the frequency and associated time period for the timer upon detection of a change of logical state between consecutive bits of the incoming data stream; and (g) repeating steps (c) through (g) for each bit in the incoming data stream.

14. The method in accordance with claim 13, wherein step (d) comprises issuing the timer based interrupt signal upon the expiration of approximately half of the countdown of the set predetermined time period for the timer.

15. The method in accordance with claim 12, wherein the continuous phase frequency shift keying processor is powered exclusively via an external RF signal generated during communication from the external device to the internal device.

16. A method for minimizing energy consumption of a continuous phase frequency shift keying modulation processor, the method comprising the steps of:

toggling an output signal of the continuous phase frequency shift keying modulation processor between a first predetermined frequency and a second predetermined frequency on a predetermined time period basis based on a logical state of each bit in an incoming data stream received as input to the continuous phase frequency shift keying modulation processor.

17. The method in accordance with claim 16, wherein the toggling step comprises the steps of:

(a) detecting a logical state of a first bit of the incoming data signal to the continuous phase frequency shift keying processor;

(b) based on the detected logical state of the first bit of the incoming data signal: (i) generating a continuous phase frequency shift keying encoded output signal at one of a first predetermined frequency or a second predetermined frequency; and (ii) setting a predetermined time period of a timer of the continuous phase frequency shift keying processor to a first time period or a second time period;

(c) generating a power down signal to toggle to a sleep mode at least some circuitry of the processor, while the timer associated with the continuous phase frequency shift keying processor remains powered on at all times;

(d) prior to the expiration of the countdown by the timer of the set predetermined time period, issuing a timer based interrupt signal to power on the previously powered down circuitry of the processor in sleep mode;

(e) monitoring the logical state of a next bit from the incoming data stream;

(f) updating the frequency and associated time period for the timer upon detection of a change of logical state between consecutive bits of the incoming data stream; and (g) repeating steps (c) through (g) for each bit in the incoming data stream.

18. The method in accordance with claim 17, wherein step (d) comprises issuing the timer based interrupt signal upon the expiration of approximately half of the countdown of the set predetermined time period for the timer.

* * * * *